(12) United States Patent
Henschel et al.

(10) Patent No.: US 11,342,717 B2
(45) Date of Patent: May 24, 2022

(54) HEADER FOR A MEDICAL IMPLANT DEVICE, PARTICULARLY FOR A PACEMAKER

(71) Applicant: BIOTRONIK SE & CO. KG, Berlin (DE)

(72) Inventors: Martin Henschel, Berlin (DE); Jan Litzke, Berlin (DE)

(73) Assignee: BIOTRONIK SE & CO. KG

( * ) Notice: Subject to any disclaimer, the term of this patent is extended or adjusted under 35 U.S.C. 154(b) by 232 days.

(21) Appl. No.: 16/577,882

(22) Filed: Sep. 20, 2019

(65) Prior Publication Data

US 2020/0014152 A1 Jan. 9, 2020

Related U.S. Application Data

(63) Continuation of application No. 15/489,874, filed on Apr. 18, 2017, now abandoned.

(51) Int. Cl.

| H01R 12/72 | (2011.01) |
|---|---|
| H01R 13/66 | (2006.01) |
| A61N 1/375 | (2006.01) |
| A61B 90/00 | (2016.01) |
| A61B 5/0205 | (2006.01) |
| A61B 5/11 | (2006.01) |

(Continued)

(52) U.S. Cl.
CPC ..... *H01R 13/6683* (2013.01); *A61B 5/02055* (2013.01); *A61B 5/11* (2013.01); *A61B 5/14532* (2013.01); *A61B 5/14542* (2013.01); *A61B 5/686* (2013.01); *A61B 7/00* (2013.01); *A61B 90/39* (2016.02); *A61N 1/375* (2013.01); *A61N 1/3718* (2013.01); *A61N 1/3752* (2013.01); *A61N 1/3756* (2013.01); *H01R 12/712* (2013.01); *H01R 13/5224* (2013.01); *H01R 13/6691* (2013.01); *H01R 24/58* (2013.01); *A61B 5/021* (2013.01); *A61B 5/08* (2013.01); *A61B 2090/367* (2016.02); *A61B 2090/376* (2016.02); *A61B 2090/3966* (2016.02); *H01R 2107/00* (2013.01)

(58) Field of Classification Search
None
See application file for complete search history.

(56) References Cited

U.S. PATENT DOCUMENTS

| 8,750,961 B1 | 6/2014 | Ries et al. |
|---|---|---|
| 8,920,198 B2 | 12/2014 | Ruschel et al. |

(Continued)

FOREIGN PATENT DOCUMENTS

| EP | 2529790 A1 | 12/2012 |
|---|---|---|
| WO | WO 2011/094413 A1 | 8/2011 |

OTHER PUBLICATIONS

European Search Report, Apln. No. 16166977.5-1666, dated Oct. 27, 2016.

*Primary Examiner* — Erica S Lee
(74) *Attorney, Agent, or Firm* — Craig A. Fieschko, Esq.; DeWitt LLP

(57) ABSTRACT

A header for a medical implant device is configured to provide an electrical connection to a circuit within the housing of the medical implant device. The header includes at least one circuit board; a header housing enclosing the circuit board and configured to be connected to the housing of the medical implant device; and a sensor system on the circuit board.

20 Claims, 7 Drawing Sheets

(51) Int. Cl.

| | | |
|---|---|---|
| *A61B 5/145* | (2006.01) | |
| *A61B 5/00* | (2006.01) | |
| *A61B 7/00* | (2006.01) | |
| *A61N 1/37* | (2006.01) | |
| *H01R 12/71* | (2011.01) | |
| *H01R 13/52* | (2006.01) | |
| *H01R 24/58* | (2011.01) | |
| *A61B 5/021* | (2006.01) | |
| *A61B 5/08* | (2006.01) | |
| *H01R 107/00* | (2006.01) | |

(56) References Cited

U.S. PATENT DOCUMENTS

| | | | |
|---|---|---|---|
| 2005/0076908 A1* | 4/2005 | Lee | A61N 1/36514 128/204.23 |
| 2007/0232119 A1 | 10/2007 | Sprain et al. | |
| 2010/0168818 A1* | 7/2010 | Barror | A61N 1/37512 607/60 |
| 2010/0241206 A1 | 9/2010 | Truex et al. | |
| 2010/0305647 A1 | 12/2010 | McCabe et al. | |
| 2011/0137414 A1 | 6/2011 | Litzke et al. | |
| 2011/0181495 A1* | 7/2011 | Chu | G09F 9/33 345/1.3 |
| 2011/0190842 A1 | 8/2011 | Johnson et al. | |
| 2012/0253440 A1* | 10/2012 | Grohmann | A61N 1/3754 607/116 |
| 2012/0309237 A1 | 12/2012 | Marzano et al. | |
| 2013/0011139 A1 | 1/2013 | Hardy et al. | |
| 2013/0183863 A1 | 7/2013 | Ruschel et al. | |
| 2013/0288501 A1* | 10/2013 | Russell | H01R 13/648 439/271 |
| 2014/0272457 A1 | 9/2014 | Watada | |
| 2015/0018912 A1* | 1/2015 | Robnett | A61N 1/36146 607/116 |
| 2015/0157853 A1* | 6/2015 | Verzal | A61N 1/3752 600/25 |
| 2015/0174409 A1* | 6/2015 | Parker | H02J 7/025 607/46 |
| 2016/0067502 A1* | 3/2016 | Bornzin | A61N 1/37241 607/116 |
| 2016/0220814 A1 | 8/2016 | Chiao | |
| 2017/0360283 A1* | 12/2017 | Kimura | H02J 50/10 |

* cited by examiner

HEADER FOR A MEDICAL IMPLANT DEVICE, PARTICULARLY FOR A PACEMAKER

CROSS-REFERENCE TO RELATED APPLICATIONS

This application is a continuation of U.S. patent application Ser. No. 15/489,874 filed Apr. 18, 2017, which claims priority under 35 USC § 119 to European Patent Application 16166977.5-1666 filed Apr. 26, 2016. Both of these prior applications are incorporated by reference herein.

FIELD OF THE INVENTION

This document concerns an invention relating generally to a header for a medical implant device, as well as to a medical implant device incorporating such a header.

BACKGROUND OF THE INVENTION

A header, also referred to as a connection housing, is used to connect electrode lines or other lines to a circuit or other electrical components of a medical implant device. Such a header usually includes a header housing which may be made out of an insulating (and preferably transparent) material, often a plastic material such as polyurethane (PU), polycarbonate (PC), and/or epoxy resin. A header of this nature is described, for example, in U.S. Pat. No. 8,676,321.

SUMMARY OF THE INVENTION

The invention, which is defined by the claims set forth at the end of this document, seeks to provide an improved header for a medical implant. An exemplary version of the invention involves a medical implant device header configured for providing an electrical connection to a circuit of the medical implant device, particularly between an electrode and a medical implant device circuit situated in a housing of the medical implant device, wherein the header includes a circuit board; a header housing which encloses the circuit board and is configured to be connected to the housing of the medical implant device; and a sensor system provided on the circuit board. (It should be understood throughout this document that where singular features are identified—e.g., "an electrode," a circuit board," etc.—more than one such feature may be included in the invention.)

By using a circuit board that can be pre-mounted with electrical components, in particular sensor systems that are usually arranged in the sealed main housing of the medical implant device, the header can achieve a higher degree of integration, allowing for easier automation of the assembly of the header and the medical implant device.

The header housing may be transparent, and can be made of the materials mentioned above, and/or of other suitable electrically insulating materials. The header housing may include an externally accessible cavity for connecting components to the header that are to be electrically connected to the medical implant device header, e.g., one or more implantable electrode lines. These lines may be intracardial or epicardial electrode lines, nerve lines, or other lines. Other components may also or alternatively be connected to the medical implant device by way of the header.

The circuit board—also referred to as "substrate"—may be made out of an insulating material, such as a ceramics (particularly biocompatible ceramics), liquid crystal polymers (LCP), polyether ether ketones (PEEK), polysulfones (PSU), or other suitable materials. Gold may be used as a material for circuit paths of the circuit board, particularly when ceramics material is used for the circuit board. Particularly, low temperature cofired ceramics (LTCC) and/or high temperature cofired ceramics (HTCC) are used as material for the circuit board.

The circuit board may include one or more layers, and may be manufactured and processed using manufacturing methods associated with molded interconnect devices (MID). Such methods include, for example, two (or multi) component injection molding, hot stamping, laser direct structuring (LDS), mask processing techniques, in-mold film laminating, and Flamecon processing. Using such methods, it is possible to apply, integrate and electrically connect features such as conductor lines, connectors and contacts (for instance IS-1/DF-1 connectors, quadrupole connectors), a neurostimulator module, sensors, antennae, X-ray markers, and/or positioning markers (for assembly), all on and/or in the circuit board.

The sensor system may be configured to measure one or more of: a quantity related to patient health status; blood glucose concentration; blood pressure; blood oxygen concentration; temperature; acceleration; patient posture; respiration; sound; and magnetic and/or electromagnetic field strength (or other field characteristics). The sensor system may also or alternatively be configured to measure an optical or chemical parameter, or a genetic quantity.

The sensor system can include sensors located in other parts of the medical implant device, such as in the device body or the electrode lines, wherein the sensor system performs measurements using one sensor, more than one sensor or a combination of sensors.

The header can include at least one antenna for receiving or transmitting signals, the antenna being integrated into the circuit board, wherein the antenna includes layers integrated into the circuit board. The antenna's receiving and transmitting capabilities can be significantly increased by including several stacked layers.

The circuit board may include color and/or symbolic markers for identifying connectors of the header.

The circuit board may include an x-ray marker for generating a defined contrast in an x-ray image of the header.

A filter for reducing electromagnetic interference, such as interference caused by radiofrequency waves or by the high frequency field of an MRI (magnetic resonance imaging) machine, may be provided on the circuit board.

A converter for converting energy induced by MRI into photonic energy may be provided on the circuit board. The converter may include a diode array for converting energy induced into the header and medical implant device into photonic energy, providing the medical implant device with improved MRI compatibility.

The circuit board may be a closed circuit board. The circuit board may include an aperture, particularly a central aperture, particularly for the arrangement of connector contact members for making connections to electrical components of the header.

The circuit board may be manufactured via three-dimensional (3D) printing techniques, whereby ceramic, metallic and/or polymer carrier materials are printed with circuit traces and features.

The circuit board may include one or more optical markers, particularly for use in automated mounting, welding, and/or other assembly processes.

The circuit board may be formed by a multicomponent molding process, preferably a two-component molding process, such as molding processes associated with molded interconnect devices (MID).

The circuit board may include contact pads for electrically connecting the circuit board to the medical implant device, particularly to the circuit of the medical implant device (e.g., to an 10o electronic control unit of the medical implant device).

The circuit board may include structures for fixation of the circuit board in the housing of the header.

The header may include an electrically conducting connection assembly electrically connected to the circuit board and configured to be connected (preferably releasably connected) to an electrode or and/or other components for providing an electrically conducting connection between the electrode(s)/components and the circuit board. The connection assembly preferably includes a DF-4 connector, an IS-4 connector, a DF-1 connector, and/or an IS-1 connector for making connection to the electrode(s)/component. The connection assembly may also include sealing, insulating and/or mounting components, preferably formed of a thermoplastic or a duroplastic material.

The connection assembly may include pins configured to be plugged into corresponding openings of the circuit board, e.g., for making electrical contact and/or for fastening the connection assembly to the circuit board. The connection assembly may be configured to be melted/fused on the circuit board for permanently fastening it to the circuit board.

The connection assembly is preferably connected to the circuit board via a connector contact 30 member, preferably a sheet metal contact member. The connection assembly may be connected to the connector contact member by means of welding, crimping, soldering, plugging, gluing, or by using spring contacts.

The circuit board may be formed as a circumferential frame defining a central aperture as described above, wherein the frame includes opposing first and second frame regions integrally connected to each other by opposing third and fourth lateral frame regions so as to form the frame shape of the circuit board surrounding the central aperture of the circuit board.

The first and second frame regions may be connected to each other by connector contact members, e.g., elongated contact strips, via which the connection assembly may be electrically connected to the circuit board. The connector contact members extend across the central aperture of the circuit board. In a preferred arrangement, the connection assembly is a DF-4 module (i.e., it forms a DF-4 connector), wherein the header then includes four connector contact members in the form of elongated contact strips that extend across the central aperture.

The header may include two additional connector contact members extending from the second frame member, which can be positioned further away from the housing of the medical implant device than the first frame region (when the header housing and the medical implant device housing are connected to each other). The additional connector contact members extend outwardly and away from the central aperture/circuit board, and are connected to an additional connection assembly forming an IS-1 connector. The connection assembly and the additional connection assembly may be integrally or otherwise connected to each other, and/or ma) form a pre-mounted assembly.

The circuit board may include a through-hole in the second frame member for fixing and/or positioning of the connection assembly (and possibly any additional connection assembly) to the circuit board.

Contact pads for electrically connecting the circuit board to the medical implant device may be provided on the first frame region.

The circuit board may be embedded in the housing of the header in a casted material, i.e., a material cast around the circuit board by injection molding or any other suitable casting process).

The invention also encompasses a medical implant device (such as a pacemaker or biomonitor) including a housing for accommodating a circuit (which may include a battery, an electronic control unit, and/or other electrical components), and a header as described above, wherein the header housing is fastened to the housing of the medical implant device.

The housing of the medical implant device may include a feedthrough by which the circuit board is electrically connected to the circuit of the medical implant device, for example, by an intermediate contact member. The medical implant device circuit may therefore be contacted from outside the medical implant device housing, which is preferably hermetically sealed, without breaking the seal of the medical implant device housing. The intermediate contact member, which may take the form of a flat or angled sheet metal member, or a sheet metal member forming a sleeve, may be connected to the circuit board and/or the feedthrough by means of welding, crimping, soldering, plugging, gluing, or by making a spring contact.

The feedthrough may be defined by a feedthrough assembly including a carrier body with a top side and a bottom side, and an electrical contact body extending from both the top side and the bottom side of the carrier body. The electrical contact body is angled and includes a first limb extending transversely to a second limb. The electrical contact body is provided on an insulating body, which can extend through the carrier body to protrude from the top side of the carrier body, and can protrude from, be flush with, or be recessed within the bottom side of the carrier body. The carrier body includes an opening next to the insulating body, wherein the opening can receive a positioning unit that locally positions the electrical contact body. The positioning unit has a lower end aligned with a bottom side of the second limb of the electrical contact body, and an upper end protruding from the top side of the insulating body. Further details on a feedthrough assembly of this nature are provided in U.S. Pat. No. 8,920,198. The feedthrough includes electrical connectors which represent separate electrical channels leading from separate electrical connections from the circuitry inside the medical implant device housing to the outside of the housing.

In an exemplary version of the medical implant device, an integrated circuit is provided on the circuit board of the header, wherein the integrated circuit is configured to control the medical implant device. The circuit in the medical implant device housing (which may be formed in whole or part of platinum) includes an energy source and/or a capacitor that may be encapsulated in the housing.

A multiplexer circuit may be provided on the circuit board of the header, with the multiplexer circuit including one or more input interfaces and output interfaces. The input interfaces may each be electrically connected to an electrical connector of the feedthrough, and each output interface may be electrically coupled to one of the electrodes of the medical implant device. When operating the medical implant, signals from the circuit located inside the medical implant device housing may be transferred via the electrical connectors of the feedthrough, through the multiplexer circuit, and to the electrodes. The multiplexer circuit is configured to switch each input interface to a designated electrical connector of the feedthrough, and switch each output interface to a designated electrode, and thereby establish the desired connection between the electrical connector of the feedthrough and the desired electrode. A multiplexer circuit of this nature can allow reduction in the number of separate electric conductors in the header and the number of electrical connectors of the feedthrough.

The multiplexer circuit may use different operational methods. It can multiplex via electrical conductors by: application of logic elements are which operate as relays; using binary encoded signals for controlling the therapy; using frequency multiplexing, for example, by using an antenna of the medical implant device (whereby data for controlling therapy can be transmitted using frequencies different from those used for RF communication); and/or via serial data exchange, e.g. similar to Universal Serial Bus (USB) data exchange. Alternatively or additionally, it can multiplex via optical methods, as by transmitting the signals through fiber optic cables or other light-transmitting elements (including through transparent apertures/passages in the feedthrough), whereby infrared (IR) or other signals can be transmitted between the circuitry inside the medical implant device housing and the header.

The feedthrough electrical connectors, multiplexer circuit, and electrodes may carry signals different from therapy signals, such as (for example) data measured by the sensors.

Preferably, the multiplexer circuit is encompassed by a biocompatible material to protect the circuit from body fluids. Exemplary materials are resins and polymer materials, such as polysulfones, silicones, or glass.

The header housing may be integrally formed with the housing of the medical implant device. In this case, the medical implant device may be a so-called leadless pacemaker and/or cardiac monitor that does not include external electrode lines, and rather uses internal electrode lines arranged in the header.

DETAILED DESCRIPTION OF EXEMPLARY VERSIONS OF THE INVENTION

Figure 1:
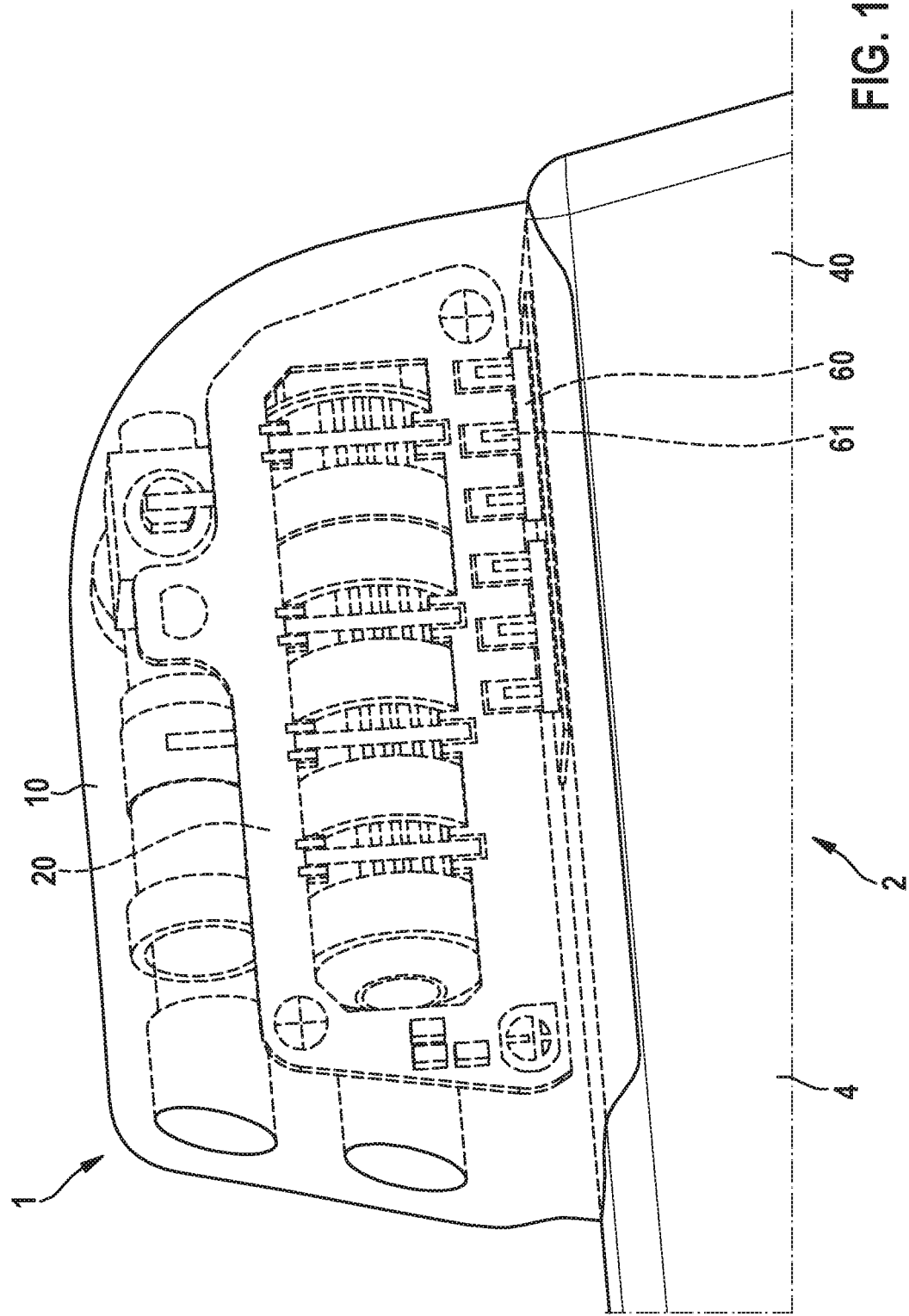
FIG. 1 shows an version of a header of a medical implant device in the form of a pace maker, wherein the header is connected to a housing of the medical implant device.

FIGS. 1-5 shows a header 1 and a medical implant device 2 exemplifying the invention. The header 1 is configured to provide an electrical connection of at least one electrode 3 (FIG. 6) to a circuit 40 (which is not shown in detail) situated in a hermetically sealed housing 4 of the medical implant device 2. The header 1 includes at least one circuit board 20, and a preferably transparent and electrically insulating header housing 10 which encloses the circuit board 20 and is configured to be connected to the housing 4 of the medical implant device 2. A sensor system 30 (FIGS. 3-4) provided on the circuit board 20 is adapted to measure at least one of the following quantities: a quantity related to patient health status; blood glucose concentration; blood pressure; blood oxygen concentration; temperature; acceleration; patient posture; respiration; sound; and magnetic and/or electromagnetic field strength (or other field characteristics)

Figure 2:
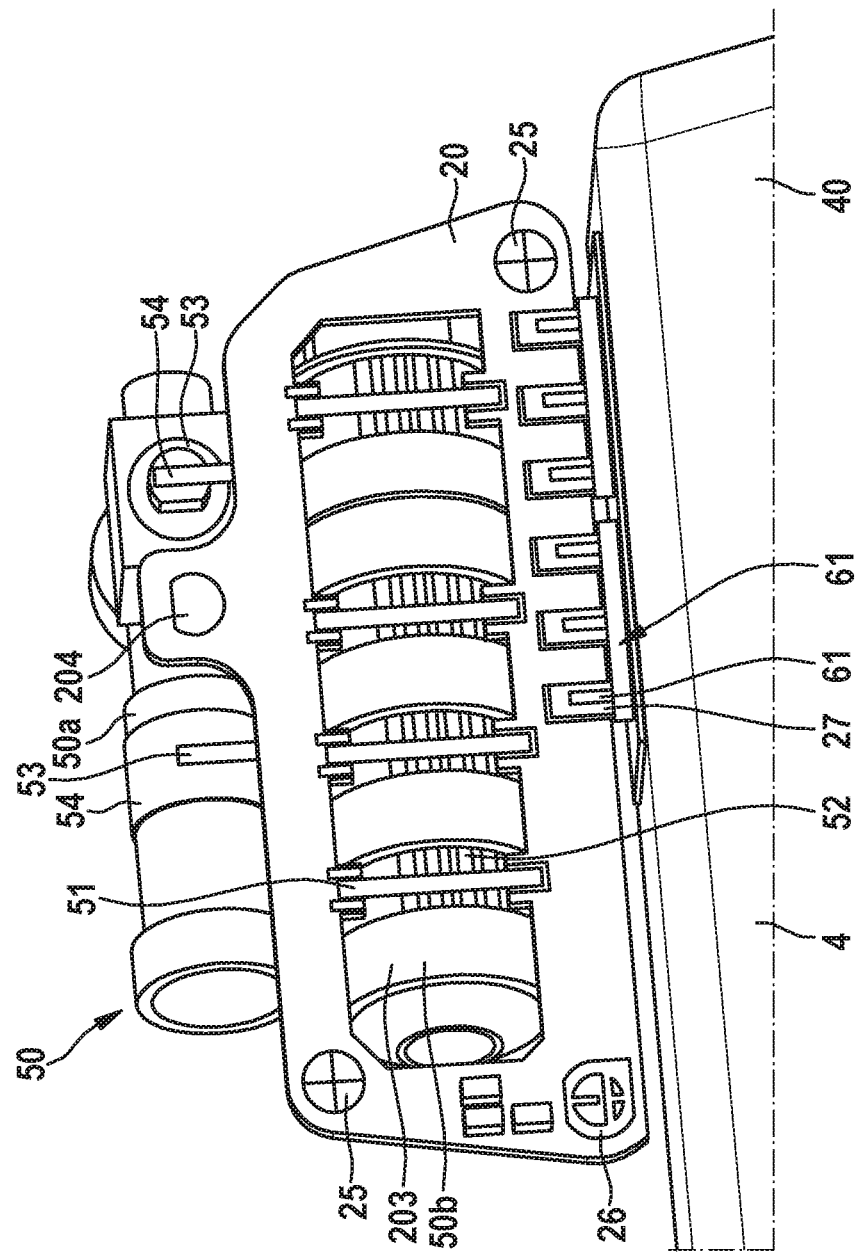
FIG. 2 shows the header according to FIG. 1 without its header housing.
Figure 3:
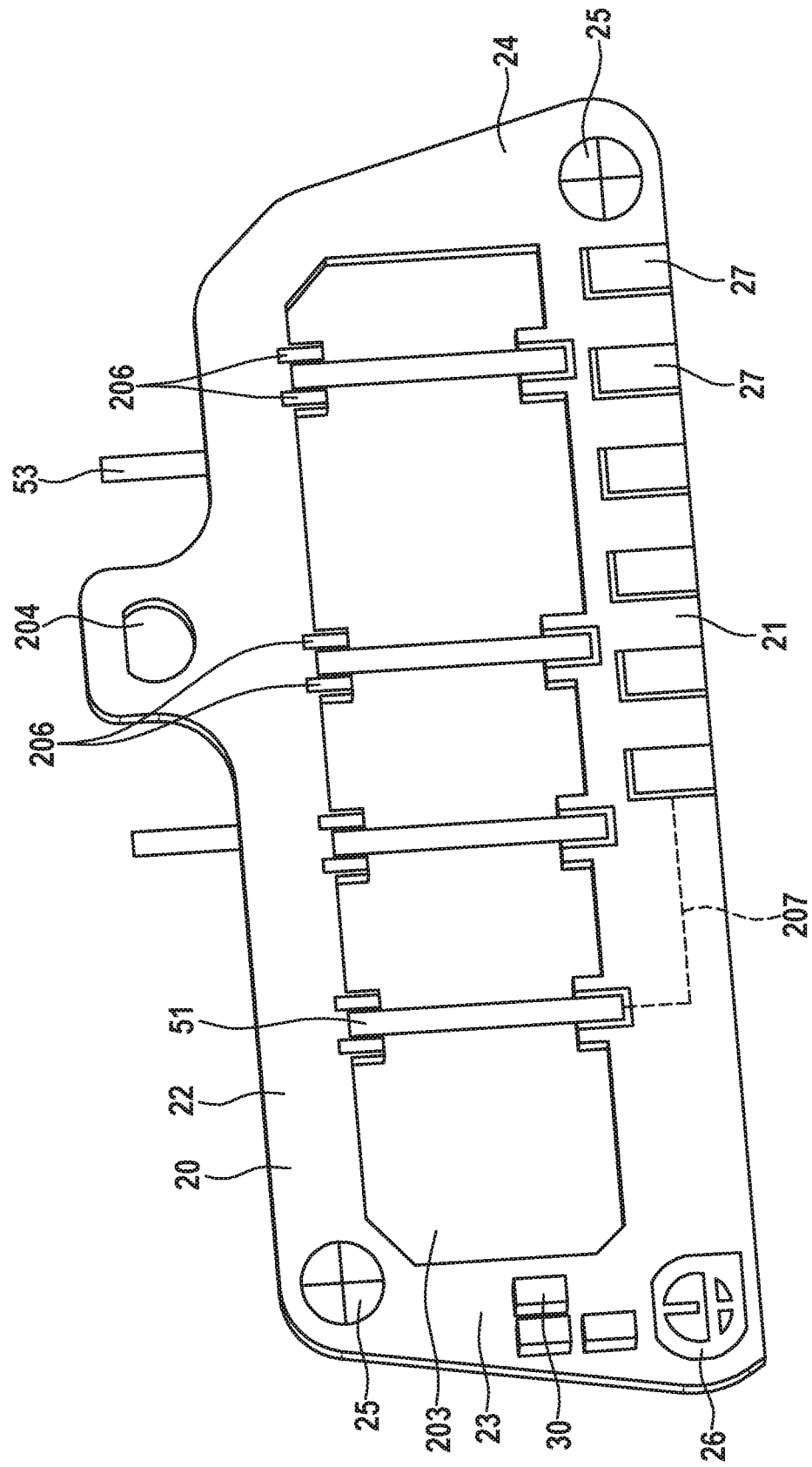
FIG. 3 shows a circuit board of the header.
Figure 4:
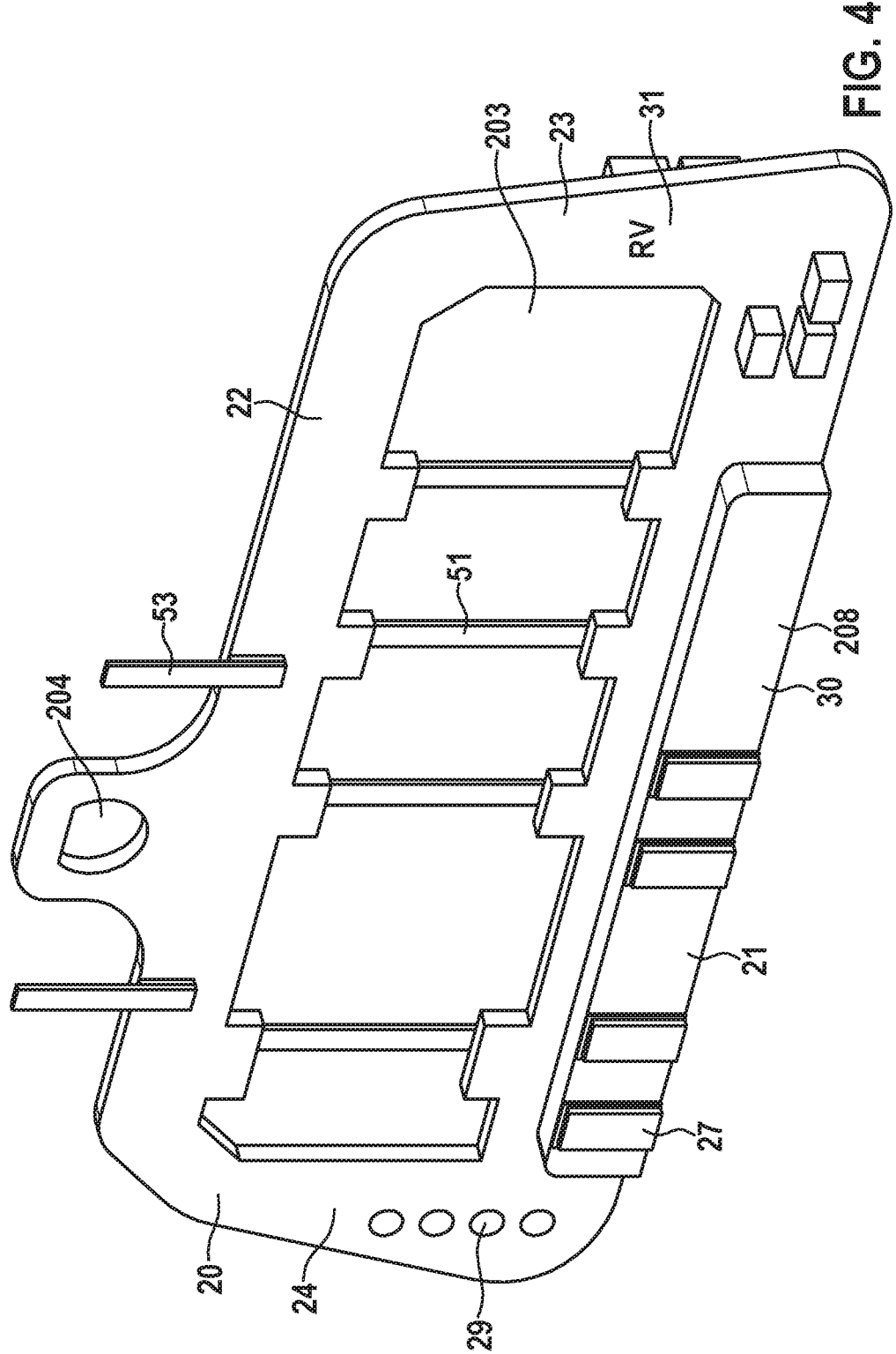
FIG. 4 shows a further illustration of the circuit board of FIG. 3.

As seen in FIGS. 1-5, the circuit board 20 is flat, and is preferably formed as a 10o circumferential frame defining a central aperture 203 (see particularly FIGS. 2-4). The circuit board 20 includes opposing first and second frame regions 21 and 22 integrally connected to each other by opposing third and fourth lateral frame regions 23, 24, with these frame regions surrounding the central aperture 203 of the circuit board 20. The circuit board 20 is preferably formed out of a low temperature cofired ceramics (LTCC) material.

FIG. 2 depicts two connection assemblies 50a, 50b that may form a pre-mounted or integrally formed connection assembly 50, and that provide (for example) a DF-4 connector 50b and an IS-1 connector 50a for connecting at least one electrode line. The circuit board 20 includes a corresponding number of connector contact members 51, 53 (FIGS. 2-5) in the form of elongated metal contact strips. To connect the circuit board 20 to the connection assembly (DF-4 connector) 50b, four of these connector contact members 51 extend from the first frame region 21 to the second frame region 22 across the aperture 203, and are welded, soldered, or otherwise connected to contacts 52 provided on the DF-4 connector 50b. The connector contact members 51 are attached to first and second frame regions 21, 22 of the circuit board 20 by means of projections 206 (FIG. 3) which hold the members 51 in place. To connect the circuit board 20 to the connection assembly (IS-1 connector) 50a, two further connector contact members 53 protrude from the second frame member 22 outwardly away from the central aperture 203, and are welded, soldered, or otherwise connected to corresponding contacts 54 (FIGS. 2, 5) of the IS-1 connector.

For fixing and/or positioning of the connector assembly 50 to the circuit board 20, the circuit board 20 includes a through-hole 204 (FIGS. 2-5) on the second frame region 22, which preferably includes a circular boundary section joined by a straight boundary section.

Figure 5:
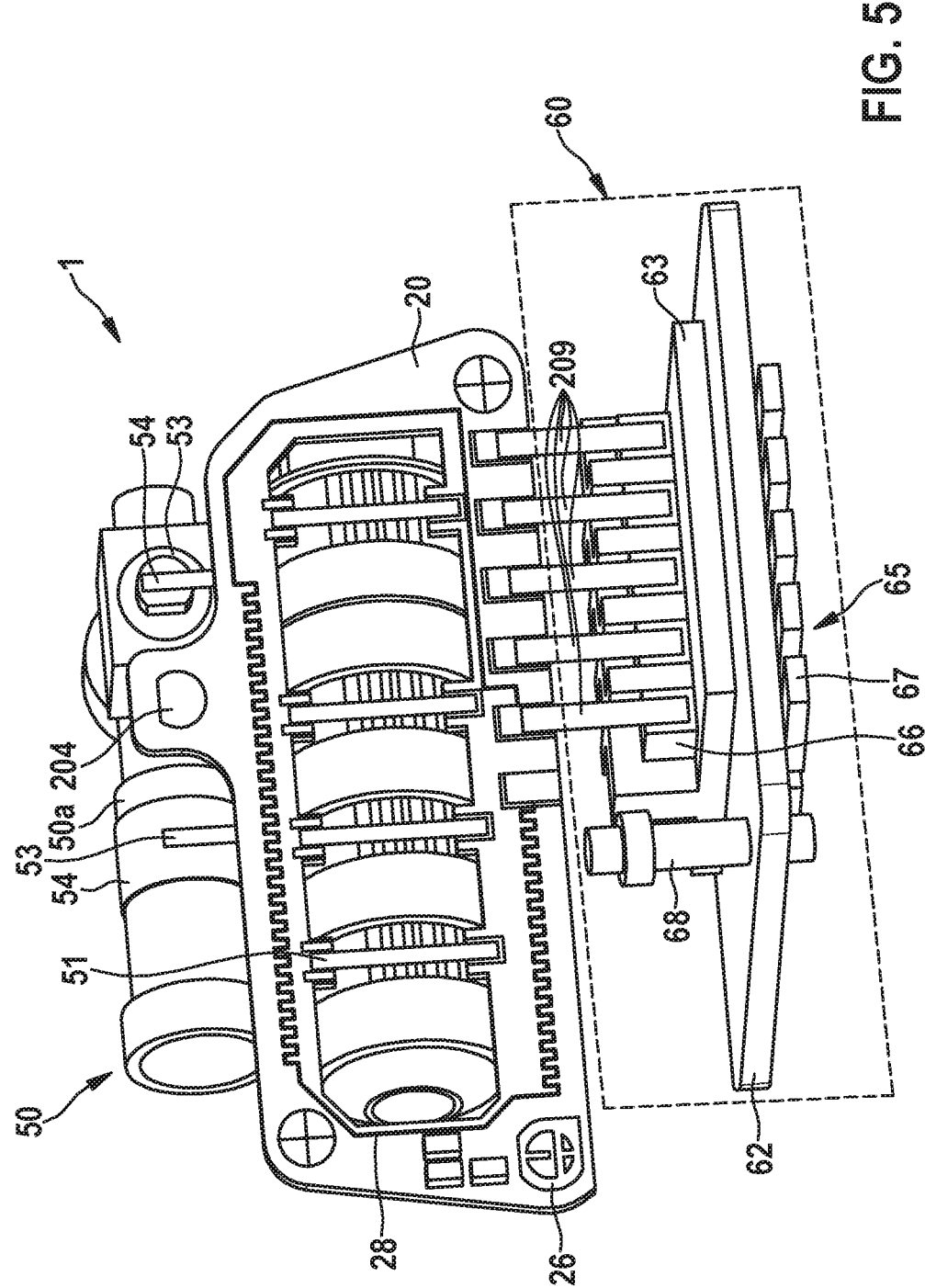
FIG. 5 shows the header according to FIGS. 1 to 4 connected to a feedthrough assembly of the medical implant device.
Figure 7:
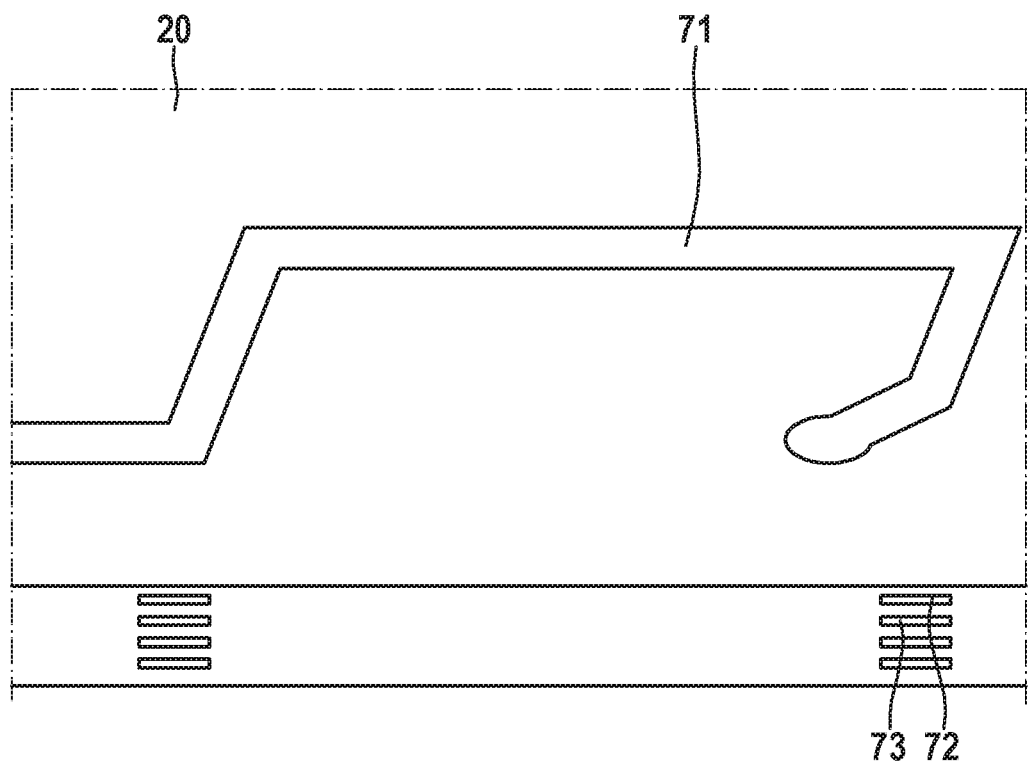
FIG. 7 shows a close up of an version of a circuit board according to the invention with a multiple layer structure.

As seen in FIG. 5, the circuit board 20 includes an antenna 28 for receiving or transmitting signals. The antenna 28 extends in a meandering path around the central aperture 203 in multiple layers of the circuit board 20. FIG. 7 shows a close-up view of an exemplary version of the circuit board 20, showing the layer structure including three layers 71, 72 and 73. Shown is a first top layer 71, where an exemplary conductor trace is depicted. The deeper layers 72 and 73 are pointed out in FIG. 7 from on the side edge of circuit board 20.

Looking to FIG. 4, the circuit board includes indicia such as color and/or symbolic markers 29, 31 for identifying the aforementioned connectors 50a, 50b of the header 1. Here the symbolic markers are implemented as alphanumeric text 31, and the color markers are implemented as light-emitting diodes 29, wherein diodes in different colors can indicate different contact states of the connectors 50a. 50b. For example, a red diode might glow when an improper contact is detected, and a green diode might glow when a proper contact has been established.

As seen in FIGS. 2, 3 and 5, the circuit board preferably includes an x-ray marker 26 for generating a defined contrast in an x-ray image of the header 1.

The header 1 preferably includes a filter on the circuit board 20 for reducing electromagnetic interference. To further improve MRI compatibility of the medical implant device 2, the header's circuit board 20 preferably also includes a converter for converting energy induced by MRI into photonic energy. The circuit board 20/converter may include a diode array for this purpose. The filter and the converter may be located at any suitable place on the circuit board 20, or may be implemented as separate components. In FIGS. 3-4, the filter and the converter are included in the sensor system 30.

As shown in FIGS. 2, 3 and 5, the circuit board 20 preferably includes optical markers 25 for use in an automated mounting and/or welding process. Here, the markers can be used to determine the position and orientation of the circuit board 20.

To electrically connect the circuit board 20 to the circuit 40 of the medical implant device 2, the circuit board 20 preferably includes contact pads 27 (FIGS. 2-4), preferably on the first frame region 21. The contact pads 27 may be connected to the connector contact members 51, preferably via internal multi-layer or single layer wiring 207 (FIG. 3) within the circuit board 20. As seen in FIG. 2, the contact pads 27 may be welded or soldered to (e.g., straight) pins 61 of a feedthrough 60 of the hermetically sealed housing 4 of the medical implant device 2, wherein the pins 61 protrude out of the housing 2 and are aligned with the contact pads 27.

As an alternative way of connecting the circuit board 20 to the circuit 40 of the medical implant device 2 in housing 4, FIG. 5 shows a version that uses a feedthrough assembly 60 as described in U.S. Pat. No. 8,920,198. The feedthrough assembly 60 includes a carrier body 62 which bears an insulating body 63, e.g., with the insulating body 63 inserted within an opening of the carrier body 62, though the carrier body 62 and insulating body 63 could be integrally or differently formed. The carrier body 62, which may be connected to a wall of the housing 4 in a sealed fashion, has a top side facing the circuit board 20 and a bottom side facing away from the top side and the circuit board 20. The insulating body 63 can be formed of a ceramic material, or alternatively a plastic or other non-conductive material.

The insulating body 63 preferably extends through the carrier body 62, protrudes above and over the carrier body top side, and also preferably projects slightly beyond the bottom side to better electrically insulate the circuit board 20 from the medical implant device (not shown). However, the bottom of the insulating body 63 could instead be aligned with the bottom side of the carrier body 62, or could extend into the opening of the carrier body 62 by a distance less than the thickness of the carrier body 62. A positioning unit 68, shown in FIG. 5 as a pin, is oriented in a direction normal to the carrier body 62 and guided through an opening in the carrier body 62. The insulating body 63 includes receptacles arranged at regular intervals along the insulating body 63 for receiving contact bodies 65. The contact bodies 65 extend towards the contact pads 27 of the circuit board 20 through the carrier body 62 and the insulating body 63. Each contact body 65 includes a first limb 66 for contacting intermediate contact members 209 (e.g., metal strips) which are in turn welded, soldered, or otherwise attached to the contact pads 27 on the circuit board 20. Further, each contact body 66 includes an integrally-connected second limb 67, wherein the second limbs 67 are used to make contact with a circuit 40 (FIG. 1, e.g., a circuit board) in the housing 4 of the medical implant device 2.

Figure 6:
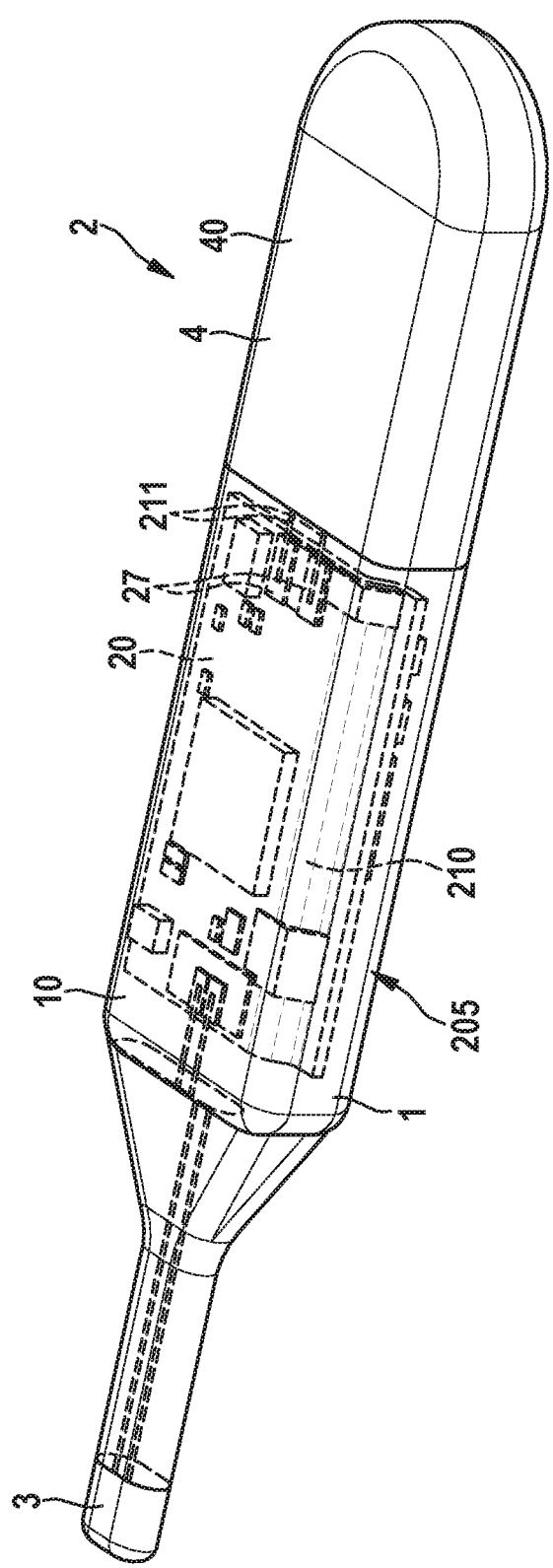
FIG. 6 shows a further version of a header/medical implant device according to the invention, wherein the header is integrally formed with the housing of the medical implant device which optionally merely houses the energy source of the device.

FIG. 6 shows another version of the header 1 and medical implant device 2, wherein here an integrated circuit 210 that controls the medical implant device 2 is transferred into the header housing 10. The header housing 10 is integrally formed with the housing 4 of the medical implant device 2, which now merely houses a battery 40 for supplying the device 2 with electrical energy. The circuit board 20 of the header 1, which is embedded in the header housing 10 in a casted material 205 cast around the circuit board 20, may be connected to the battery 40 via contact pads and metal strips extending therefrom. The electrode 3 is integrated into the header housing 10 so that the electrode lines extend within the header housing 10. Such an arrangement can be used as a so-called leadless pacemaker and/or biomonitor.

The foregoing versions of the invention are exemplary, and are presented for purposes of illustration only. Alternative versions may include some or all of the features described herein. The invention is not limited to the foregoing versions, and rather is limited only by the claims set out below, with the invention encompassing all different versions that fall literally or equivalently within the scope of these claims.

What is claimed is:

1. A header (1) for a medical implant device (2), the medical implant device (2) having a housing (4) with a device circuit (40) therein, wherein:
   a. the header (1) includes:
      (1) a header housing (10) configured to be connected to the housing (4) of the medical implant device (2),
      (2) a circuit board (20) enclosed within the header housing (10), the circuit board (20) having a sensor system (30) thereon,
      (3) a connector (50a, 50b):
         (a) connected to the circuit board (20), and
         (b) configured to electrically connect to a lead terminal,
      (4) a connector contact member (51, 53):
         (a) electrically connecting the connector (50a, 50b) to the circuit board (20), and
         (b) extending from the circuit board (20):
            i. at least substantially parallel to or coincident with a board plane in which a major portion of the circuit board (20) is situated,
            ii. to connect with the connector (50a, 50b) at a location spaced from the circuit board (20),
   b. the header (1) is configured to provide an electrical connection between the circuit board (20) and the device circuit (40) of the medical implant device (2), and
   wherein the circuit board (20):
   a. extends along the board plane between opposing first and second board ends (21, 22),
   b. includes contact pads (27) situated at or adjacent the first board end (21), the contact pads (2) being electrically connected to the circuit board (20),
   c. the connector (50a) is connected to the circuit board (20) at or adjacent the second board end (22).

2. The header (1) of claim 1 wherein the sensor system (30) is configured to measure at least one of the following quantities:
   a. a quantity related to patient health status,
   b. blood glucose concentration,
   c. blood pressure, d. blood oxygen concentration,
e. temperature,
f. acceleration,
g. patient posture,
h. respiration,
i. sound,
j. magnetic field characteristics,
k. electromagnetic field characteristics.

3. The header (1) of claim 1 further including at least one antenna (28):
   a. configured to receive or transmit signals,
   b. provided on the circuit board (20), and
   c. wherein the antenna (28) is defined by layers spaced at different locations across a thickness of the circuit board (20), the thickness being oriented perpendicular to the board plane.

4. The header (1) of claim 1 wherein the connector (50a, 50b) is defined by one of:
   a. a DF-4 connector (50b),
   b. an IS-4 connector,
   c. a DF-1 connector, and
   d. an IS-1 connector (50a).

5. The header (1) of claim 1 wherein:
   a. an aperture (203) is defined within the circuit board (20), and
   b. the connector contact member (51) extends from the circuit board (20) from and between opposing sides of the aperture (203), while leaving the aperture (203) unobstructed on opposing sides of the connector contact member (51).

6. The header (1) of claim 1 wherein:
   a. the circuit board (20) is bounded by a board perimeter in the board plane,
   b. the connector contact member (53):
      (1) extends from the board perimeter, and
      (2) connects to the connector (50a) at a location spaced from the board perimeter.

7. The header (1) of claim 1 wherein:
   a. an aperture (203) is defined within the circuit board (20) between the first and second board ends (21, 22), and
   b. a second connector (50b) is:
      (1) situated within the aperture (203), and
      (2) connected to the circuit board (20),
      the second connector being configured to electrically connect to a second lead terminal.

8. The header (1) of claim 1 wherein the circuit board (20) has indicia defined on a discrete subsection of the circuit board (20), the indicia identifying a characteristic of the connector (50a, 50b).

9. The header (1) of claim 1 wherein the circuit board (20) includes an x-ray marker (26) configured to generate a defined contrast in an x-ray image of the header (1).

10. The header (1) of claim 1 further including a converter configured to convert magnetic resonance imaging energy received by the header (1) into photonic energy.

11. The header (1) of claim 1 wherein casted material (205) encapsulates the circuit board (20) within the header housing (10).

12. The header (1) of claim 1 further including a medical implant device (2) having a housing (4) with a device circuit (40) therein, wherein the header housing (10) is connected to the housing (4) of the medical implant device (2).

13. The header (1) of claim 12 wherein:
   a. the circuit board (20) has a header circuit (210) thereon configured to control the medical implant device (2), and
   b. the device circuit (40) in the housing (4) includes at least one of:
      (1) a battery configured to power stimulation pulses, and
      (2) a capacitor configured to generate stimulation pulses.

14. The header (1) of claim 1 wherein:
   a. the connector contact member (51, 53) is defined by an elongated member,
   b. at least a portion of the length of the connector contact member (51, 53) between the circuit board (20) and the connector (50a, 50b) is unconnected to either of the circuit board (20) and the connector (50a, 50b).

15. A combination medical implant device (2) and header (1) including:
   a. a medical implant device (2) having a housing (4) with a device circuit (40) therein, the device circuit (40) including at least one of:
      (1) a battery configured to power stimulation pulses, and
      (2) a capacitor configured to generate stimulation pulses,
   b. a header (1) for the medical implant device (2), the header (1) including:
      (1) a header housing (10) configured to connect to the housing (4) of the medical implant device (2), and
      (2) a circuit board (20) enclosed within the header housing (10), the circuit board (20):
         (a) having at least a major portion thereof situated along a board plane,
         (b) having a header circuit (210) thereon configured to control the device circuit (40) of the medical implant device (2),
      (3) a connector (50a, 50b) configured to electrically connect to a lead terminal,
      (4) a connector contact member (51, 53):
         (a) electrically connecting the connector (50a, 50b) to the circuit board (20), and
         (b) extending from the circuit board (20),
            i. at least substantially parallel to or coincident with the board plane,
            ii. to connect with the connector (50a, 50b) at a location spaced from the circuit board (20),
      wherein the header (1) provides an electrical connection between the header circuit (210) and the device circuit (40) of the medical implant device (2) when the header housing (10) is connected to the housing (4) of the medical implant device (2).

16. The combination of claim 15 wherein:
   a. an aperture (203) is defined within the circuit board (20), and
   b. the connector contact member (51) extends from the circuit board (20) from and between opposing sides of the aperture (203), while leaving the aperture (203) unobstructed on opposing sides of the connector contact member (51).

17. The combination of claim 15 wherein:
   a. the circuit board (20) is bounded by a board perimeter in the board plane,
   b. the connector contact member (53):
      (1) extends from the board perimeter, and
      (2) connects to the connector (50a) at a location spaced from the board perimeter.

18. The combination of claim 15 wherein the circuit board (20):
   a. extends along the board plane between opposing first and second board ends (21, 22), b. includes contact pads (27) situated at or adjacent the first board end (21), the contact pads (2) being electrically connected to the circuit board (20), c. the connector (50*a*) is connected to the circuit board (20) at or adjacent the second board end (22).

19. The header (1) of claim 15 wherein:

a. the connector contact member (51, 53) is defined by an elongated member, b. at least a portion of the length of the connector contact member (51, 53) between the circuit board (20) and the connector (50*a*, 50*b*) is unconnected to either of the circuit board (20) and the connector (50*a*, 50*b*).

20. A header (1) for a medical implant device (2), the medical implant device (2) having a housing (4) with a device circuit (40) therein, wherein:

a. the header (1) includes:

(1) a header housing (10) configured to be connected to the housing (4) of the medical implant device (2), (2) a circuit board (20) enclosed within the header housing (10), the circuit board (20) having a sensor system (30) thereon, (3) a connector (50*a*, 50*b*) configured to electrically connect to a lead terminal, (4) a connector contact member (51, 53):

(a) extending from the circuit board (20) at least substantially parallel to or coincident with a board plane in which a major portion of the circuit board (20) is situated, (b) connected to the connector (50*a*, 50*b*) at a location spaced from the circuit board (20), and (c) electrically connecting the connector (50*a*, 50*b*) to the circuit board (20), b. the header (1) is configured to provide an electrical connection between the circuit board (20) and the device circuit (40) of the medical implant device (2).

* * * * *